(12) United States Patent
Cernica

(10) Patent No.: US 9,370,668 B2
(45) Date of Patent: Jun. 21, 2016

(54) APPARATUS AND METHOD TO VISUALLY VIEW HIGH-DOSE-RADIATION APPARATUS USED TO VERIFY QUALITY ASSURANCE

(75) Inventor: George Dumitru Cernica, Fairfax, VA (US)

(73) Assignee: BEST CURE FOUNDATION, Inc., Springfield, VA (US)

( * ) Notice: Subject to any disclaimer, the term of this patent is extended or adjusted under 35 U.S.C. 154(b) by 346 days.

(21) Appl. No.: 13/333,404

(22) Filed: Dec. 21, 2011

(65) Prior Publication Data

US 2013/0165731 A1 Jun. 27, 2013

(51) Int. Cl.
| | | |
|---|---|---|
| *A61N 5/00* | (2006.01) | |
| *A61M 36/00* | (2006.01) | |
| *A61N 5/10* | (2006.01) | |

(52) U.S. Cl.
CPC ............... *A61N 5/00* (2013.01); *A61N 5/1075* (2013.01); *A61N 2005/1008* (2013.01)

(58) Field of Classification Search
CPC   A61N 5/00; A61N 2005/1008; A61N 5/1075
USPC ........... 600/1–8; 250/252.1; 378/45, 543, 54, 378/65, 87, 88, 108; 73/1.01; 604/59–64; 702/28, 40, 49, 85, 89, 94, 95, 97, 104
See application file for complete search history.

(56) References Cited

U.S. PATENT DOCUMENTS

| | | | | |
|---|---|---|---|---|
| 5,561,698 | A * | 10/1996 | Mick et al. ..................... | 378/162 |
| 6,064,976 | A * | 5/2000 | Tolopka ....................... | 705/7.13 |
| 6,869,390 | B2 * | 3/2005 | Elliott et al. ...................... | 600/1 |
| 7,097,609 | B2 * | 8/2006 | Kindlein et al. .................. | 600/7 |
| 2006/0249679 | A1 * | 11/2006 | Johnson et al. ............... | 250/332 |
| 2009/0093685 | A1 * | 4/2009 | Vu et al. ........................ | 600/300 |
| 2011/0117025 | A1 * | 5/2011 | Dacosta et al. ................ | 424/9.6 |

FOREIGN PATENT DOCUMENTS

WO   WO2012034157 A1 *   3/2012

OTHER PUBLICATIONS

Wilkinson, DA, "High dose rate (HDR) brachytherapy quality assurance: a practical guide," Biomed Imaging Interv J. Apr.-Jun. 2006; 2(2).*
ESTRO: A Practical Guide to Quality Control of Brachytherapy Equipment.*

* cited by examiner

*Primary Examiner* — Charles A Marmor, II
*Assistant Examiner* — Joshua D Lannu

(57) ABSTRACT

An apparatus for testing a high-dose-rate afterloader machine comprising an image capturing device that used to capture a plurality of still images or a real-time video, wherein said image capturing device further comprises, a zoom lens, a microphone and a light, a measurement ruler that is located on a base plate; a plurality of calibration points located on the said base plate, a source insert that connects to said high-dose-rate afterloader machine to one end, wherein said source insert allows entry of a radioactive pellet and a source wire into one end, and an adjustable shaft that is connected to said base plate and connected to said image capturing device.

23 Claims, 13 Drawing Sheets

APPARATUS AND METHOD TO VISUALLY VIEW HIGH-DOSE-RADIATION APPARATUS USED TO VERIFY QUALITY ASSURANCE

FIELD OF THE INVENTION

The invention generally relates to a method and an apparatus for a visual detection device and a sound detection device to ascertain the positional, temporal accuracy of an afterloader machine or afterloader device through the use of software calculations in addition to determining the activity of the radioactive source through use of the radiation detectors placed within the device or by image processing, to visually and audibly monitor a patient treatment delivery and ascertain its accuracy, to visually and audibly ascertain the positional and temporal accuracy of a patient high dose rate brachytherapy radiation plan.

BACKGROUND

Brachytherapy, also known as internal radiotherapy, sealed source radiotherapy, curietherapy or endocurietherapy, is a form of radiotherapy where a radiation source is placed inside or next to the area requiring treatment either permanently or temporarily. The two most common forms of brachytherapy are Low-Dose-Radiation (hereafter referred to as "LDR") and High-Dose-Radiation (hereafter referred to as "HDR"). Prior systems, in the HDR treatment, the radioactive source is located in an afterloader machine. The afterloader machine contains a single highly radioactive pellet at the end of a wire. The pellet is pushed into each of the catheters one by one under a computer control. The computer system is operated by medical personnel who control the afterloader machine to determine the amount of time the pellet stays in each catheter and also determines the location of the pellet as predetermined by a radiation plan and radiation prescription. With a few well-placed catheters in or near the target, HDR brachytherapy can provide a very precise and effective treatment that takes only a few minutes. In contrast to LDR brachytherapy where treatment may take up 2 to 3 days or external beam radiation which can take up to 6 weeks, the HDR treatment is delivered over a period of minutes, either for a single treatment, or a plurality of treatments as prescribed by the radiation oncologist. This type of treatment has many benefits, since the afterloader controls the radiation source, and radiation exposure to the patient, doctors, and hospital staff is reduced. After the HDR treatment, the pellet retracts into the afterloader. The patient is not exposed to radiation. However, a disconcertingly larger number of misadministration of radiation with HDR machines have been documented. Specifically, if a pellet is programmed to dwell at a position not indicated by the prescription, the patient will receive a large dose of radiation to healthy tissue and not receive any therapeutic radiation to the targeted region, and likely injuring the patient. Therefore, there is a need to have a device that can report a problem with the programming of the HDR machine. Additionally, federal and state law dictate that HDR machines must be tested every day prior to treatment, and every month. Currently, the tests are done through the use of either radiochromic film or radiographic film. Radiographic film requires the radioactive pellet to be programmed to dwell at a specific position on the film. The film is then developed, and the positional accuracy ascertained subsequently. With radiochromic film, the procedure is identical except that the film does not require development. Both quality assurance procedures incur significant costs as radiochromic film is expensive, and a film development room is expensive to maintain. Additionally, this quality assurance routine is contraindicative of the federal mandate to transition to a paperless hospital environment. Hence, there is a need in the art for a digital, cost-effective solution to the quality assurance of the HDR unit.

The afterloader machine has many different parts. Currently, the afterloader machine has a computer control, a vault, a driving system that is connected to the computer control, a plurality of connection ports that is attached to transfer tubes, and cable wires or solid metal wires. The afterloader machine has a long cable wire or solid metal wire attached to a radioactive source located inside the vault. The computer system will initiate the drive system, which is a very large motor that pushes the metal wire outside of the connection port and then into a transfer tube and eventually to a catheter inserted in a patient for irradiation. The vault is located at the base, and is the starting point from where the driving system pushes out the cable wire or solid metal wire outside the connection ports. The vault is a shielded container designed to protect individuals from radiation of the pellet while no treatment is being delivered. The computer system can push a single or multiple wires concurrently into the catheter therefore irradiating a volume. The afterloader can place a radioactive pellet within less than one millimeter accuracy, but its accuracy must be confirmed prior to patient treatments, every month, and every time maintenance operations are performed on the unit as per federal and state regulations. Since the pellet's radioactivity will decay, source changes occur every two to six months. After every source change, a large number of tests must be performed to ascertain the accuracy of the device has not been compromised. Therefore, one of ordinary skill in the art would appreciate a system that can test the pellets that have being changed in the afterloader.

Current methods in ascertaining the spatial accuracy of the radioactive pellet implement the use of radiographic or radiochromic film. In either case, the film is placed on a ruler-based jig and the radioactive pellet is sent into the jig for a predetermined time. The radiation darkens the film, which is then analyzed that the darkening is in the correct place. Both films suffer from costs (radiochromic film is expensive while radiographic film requires a film development dark room with regular maintenance). Additionally, whereas the procedure allows for a qualitative pass-fail assessment, a quantitative measurement of the accuracy of the pellet placement cannot be readily ascertained.

Government regulations such as 10 CFR Part 35, Medical Use of a Byproduct Material require facilities to test the temporal and positional accuracy of the pellet prior to patient treatments. With using radiocromic or radiographic film for testing, significant costs are incurred due to the time and equipment necessary to satisfy the mandate. Therefore, there is a need to one of ordinary skill in the art to have a testing machine that can quickly test HDR afterloader precision while reducing the cost of regulated government testing.

Also to maintain government licenses, each facility is required to produce documentation for required testing. Film inherently decomposes over time, and hence the testing record can be compromised. Additionally, film and film development equipment is expensive to obtain and to maintain, additionally, by having film as the testing device, a digital record of the testing is highly inconvenient due the necessitation of scanning the films. All these factors result in additional expenditures to maintain records and perform the necessary tests, and indirectly affect the patients' treatment costs. Therefore, one of ordinary skill in the art would appreciate a need for a digital system that conveniently stores, records and performs all the necessary testing prior to patient delivery.

SUMMARY OF INVENTION

According to one general aspect, an apparatus for testing a high dose rate afterloader machine comprising an image capturing device that is used to capture a plurality of still images or a real-time video, wherein said image capturing device further comprises, an optional zoom lens, a microphone, an optional light source, a measurement ruler that is located on a base plate, a plurality of calibration points located on the said base plate, a source insert that connects to said high-dose-rate afterloader machine to one end, wherein said source insert allows entry of a radioactive pellet and a source wire into one end, and an adjustable shaft that is connected to said base plate and connected to said image capturing device.

In addition, the apparatus for calibrating said high-dose-rate afterloader machine or afterloader device further comprising said base plate may contain a plurality of source inserts, and wherein, said image capturing device may make measurements, simultaneously or individually, for each said pellet and said source wire. Further, the apparatus for calibrating said high-dose-rate afterloader machine further comprising said image capture device communicates with said microphone and uses information from both said image capture device and said microphone to adjust said high-dose-rate afterloader machine. Also, the apparatus for calibrating a high-dose-rate afterloader machine further comprises, a transition-in-timer, wherein said transition-in-timer is associated with said image capture device, a dwell timer, wherein said dwell timer is associated with to said image capture device and said microphone, and a transition-out-timer, wherein said transition-out-timer is associated with said microphone. In addition, the apparatus for testing a high-dose-rate afterloader machine further comprises, a battery, wherein, said battery is connected to said image capture device, and a wireless transmitter, wherein, said wireless transmitter communicates all the information from said image capture device, said light, said zoom lens, and said microphone.

In another general aspect, there is provided a method of testing in real-time a high-dose-rate afterloader apparatus or afterloader device comprising enabling an apparatus, initiating self-calibration and testing all functional equipment, acquiring one or more images from an image capture device, monitoring sound levels from a microphone, starting a transition-in-timer when a sound level reaches above a predetermined threshold value, ending said transition-in-timer and simultaneously starting a dwell timer, ending said dwell timer and simultaneously starting a transition-out-timer; and deactivating said image capturing device. Also, in the method for testing in real-time a high-dose-rate afterloader apparatus, wherein said transition-in-timer further comprises running the transition-in-timer until motion is detected by said image capture device. Further, in the method for testing in real-time a high-dose-rate afterloader apparatus or afterloader device, wherein said dwell timer further comprises capturing images at a predetermined interval, performing image noise analysis, and running the dwell timer until sound is detected above a predetermined threshold value by a sound detection device or sound detector, such as said microphone. In addition, in the method for testing in real-time a high-dose-rate afterloader apparatus, wherein said transition-out-timer further comprises running said transition-out-timer until sound is detected below a predetermined threshold value by said microphone.

In another general aspect there is provided a method of post-analysis for testing a high-dose-rate afterloader apparatus comprising enabling an apparatus, initiating self-calibration and testing all functional equipment, acquiring one or more images from a image capture device, deactivating said image capturing device, loading said one or more images for analysis, monitoring sound levels from a microphone during said analysis of one or more images, starting a transition-in-timer when a sound level reaches above predetermined threshold value during said analysis of one or more images, ending said transition-in-timer and simultaneously starting a dwell timer during said analysis of one or more images, and ending said dwell timer and simultaneously starting a transition-out-timer during said analysis of one or more images. In addition, the method post-analysis for testing a high-dose-rate afterloader apparatus wherein said transition-in-timer further comprises running transition-in-timer until motion is detected by said image capture device. Further, the method of post-analysis for testing a high-dose-rate afterloader apparatus wherein said transition-in-timer further comprises capturing images at a predetermined interval, performing image noise analysis, and running dwell timer until sound is detected above a predetermine threshold value by said microphone. Also, the method post-analysis for calibrating a high-dose-rate afterloader apparatus wherein said transition-in-timer further comprises running said transition-out-timer until sound is detected below a predetermined threshold value by said microphone.

In another general aspect there is provided a non-transitory computer readable medium comprising a computer program stored thereon to test a high-dose-rate afterloader device, the computer program comprising a set of instructions that, when executed by a computer, causes the computer to perform the following operations enabling an apparatus, initiating self-calibration and testing all functional equipment, acquiring one or more images from a image capture device, monitoring sound levels from a microphone, starting a transition-in-timer when a sound level reaches above predetermined threshold value, ending said transition-in-timer and simultaneously starting a dwell timer, ending said dwell timer and simultaneously starting a transition-out-timer; and deactivating said image capturing device. In addition, the non-transitory computer readable medium relating to the computer program further comprises instructions that, when executed by the computer, causes the computer to perform the following operations of running transition-in-timer until motion is detected by said image capture device. Also, the non-transitory computer readable medium relating to the computer program further comprises instructions that, when executed by the computer, causes the computer to perform the following operations capturing images at a predetermined interval, performing image noise analysis, and running dwell timer until sound is detected above a predetermine threshold value by said microphone. Further, the non-transitory computer readable medium relating to the computer program further comprises instructions that, when executed by the computer, causes the computer to perform the following operations running said transition-out-timer until sound is detected below a predetermined threshold value by said microphone.

In another general aspect there is provided a non-transitory computer readable medium comprising a computer program stored thereon to calibrate a high-dose-rate afterloader device, the computer program comprising a set of instructions that, when executed by a computer, causes the computer to perform the following operations enabling an apparatus, initiating self-calibration and testing all functional equipment, acquiring one or more images from a image capture device, deactivating said image capturing device, loading said one or more images for analysis, monitoring sound levels from a microphone during said analysis of one or more images, starting a transition-in-timer when a sound level reaches above predetermined threshold value during said analysis of one or more images, ending said transition-in-timer and simultaneously starting a dwell timer during said analysis of one or more images, and ending said dwell timer and simultaneously starting a transition-out-timer during said analysis of one or more images. In addition, the non-transitory computer readable medium relating to the computer program further comprises instructions that, when executed by the computer, causes the computer to perform the following operations of running transition-in-timer until motion is detected by said image capture device. Also, the non-transitory computer readable medium relating to the computer program further comprises instructions that, when executed by the computer, causes the computer to perform the following operations capturing images at a predetermined interval, performing image noise analysis, and running dwell timer until sound is detected above a predetermine threshold value by said microphone. Furthermore, the non-transitory computer readable medium relating to the computer program further comprises instructions that, when executed by the computer, causes the computer to perform the following operations running said transition-out-timer until sound is detected below a predetermined threshold value by said microphone.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as to be defined by claims to be filed in a non-provisional application.

DETAILED DESCRIPTION

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The invention generally relates to a high dose rate brachytherapy afterloader. Through the use of a visual detector (such as a camera) and through the use of software, the positional accuracy of the device can be verified without the use of film. The addition of radiation detectors in the device can also then evaluate the source activity, and confirm the position of the radioactive source.

Figure 1:
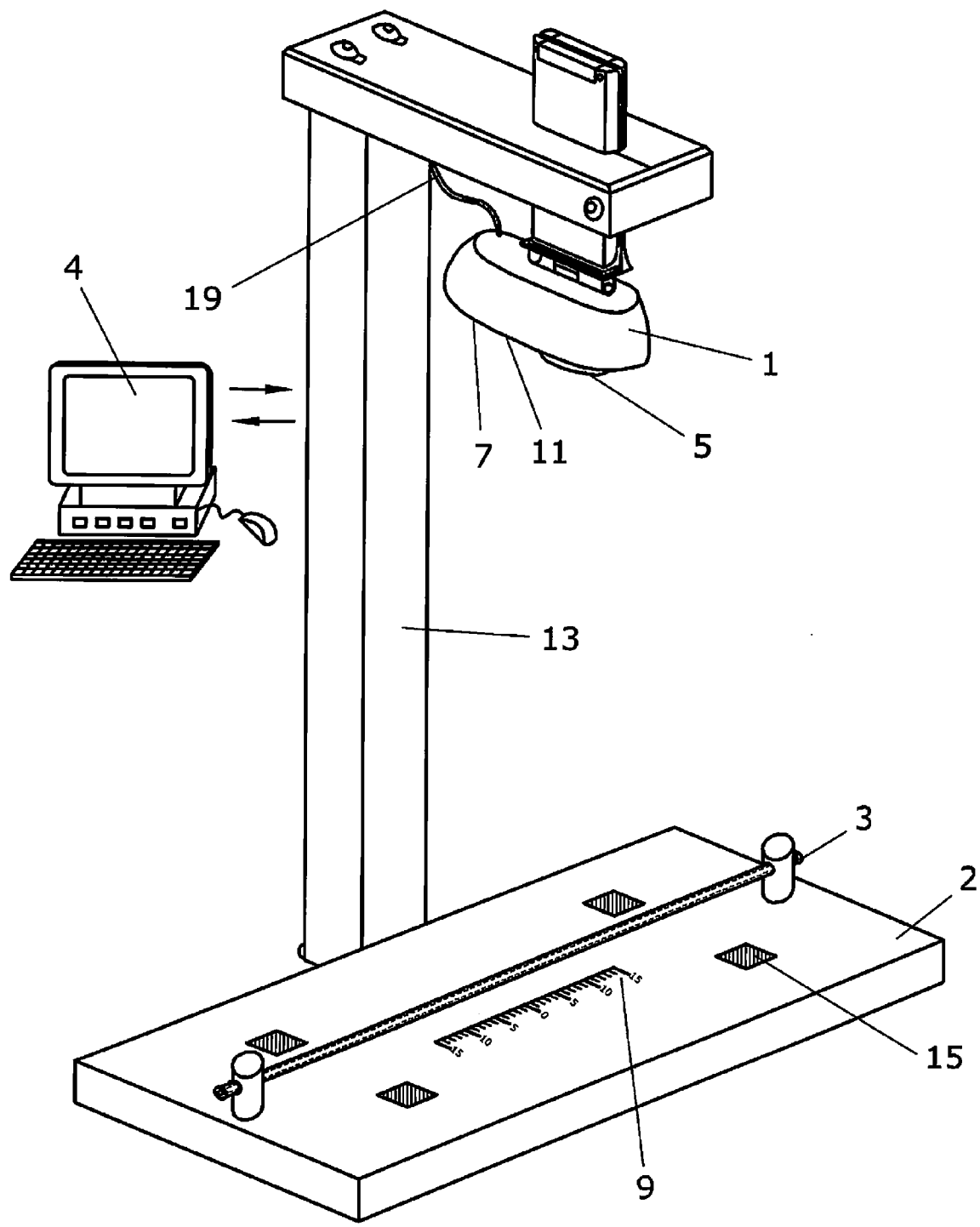
FIG. 1 illustrates a front view of the apparatus.

FIG. 1 illustrates a front view of the apparatus. The apparatus includes a digital camera 1 that directly overlooks the source insert 3. The source insert 3 is located on the base plate 2. The base plate 2 is used to hold the source wire with the pellet. The source insert 3 is supposed to be clear plastic that allows the source wire to be measured against the measurement ruler 9. The source insert is connected to the transfer tube that is connected to the after loader machine. The measurement ruler 9 will give the user a physical and tangible confirmation of the computer's calculated pellet position. Further, the base plate 2 contains a plurality of calibration points 15. The calibration points 15 are used to perform self-calibration tests and self-consistency tests to confirm the integrity of the device, in addition to image noise analyses. The base plate 2 is connected to the adjustment shaft 13. The adjustment shaft 13 may be adjusted to vary in size. The adjustment shaft 13 is connected to the digital camera 1, which is used to capture video or a series of still images. The digital camera 1 has a zoom lens 5 so that the system may zoom into the source insert 3 in real-time for precise testing or for focusing purposes. The digital camera 1 also contains a light 7, which is used to illuminate clearly the field of view. This light 7 provides a contrast to the back of the base plate 2 as well as allows the digital camera 1 to have proper visibility. The digital camera 1 is also associated with a sound detection device or sound detector, such as a microphone 11. The microphone 11 takes into the account the sound from the afterloader device. The microphone, digital camera 1, light 7, zoom lens 5 and afterloader device are all connected to the computer 4. The computer operation of the apparatus for calibrating a high-dose-rate afterloader including the digital camera 1, the light 7, the zoom lens 5, the microphone 11 and the timer operation, as well as the computer operation of the afterloader device, by the computer 4 will be discussed below.

Figure 2:
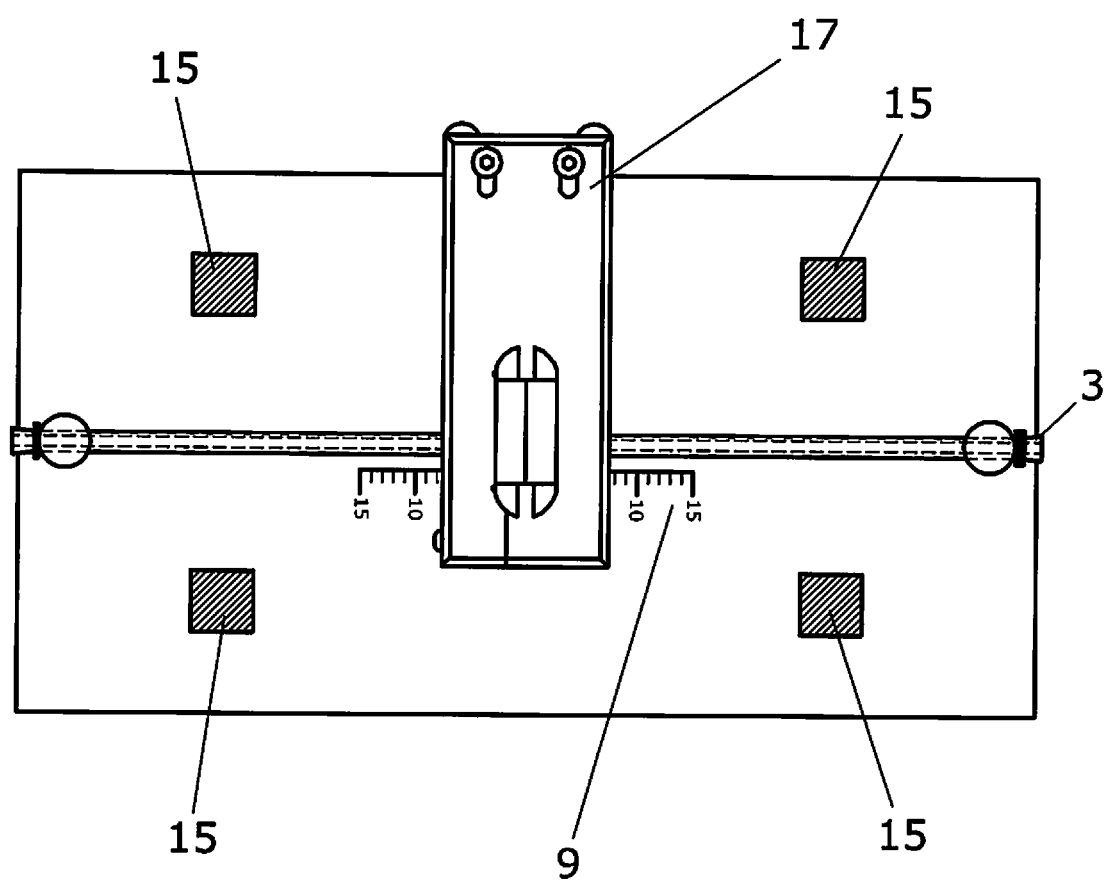
FIG. 2 illustrates a top view of the apparatus.

FIG. 2 illustrates the top view of the apparatus. The top view demonstrates the angular view of the apparatus. On top is the camera lock 17. The camera lock 17 is used to fix the digital camera in place and to center the digital camera in the middle of the measurement ruler 9. By looking downward, the digital camera will have an aerial perspective of the source wire and pellet. A computer program can capture the video or series of images and determine the location of the source pellet, and see if the motor in the afterloader device is pushing the source wire and pellet to the programmed location accurately. The ruler is used to provide the user a visual assessment of the source position accuracy to correlate to the computer-calculated position accuracy. The source insert 3 can be connected to the transfer tube; the transfer tube may be connected to either side of the apparatus, since both sides are open. In addition, the calibration points 15 are used to center the apparatus to the afterloader.

Figure 3:
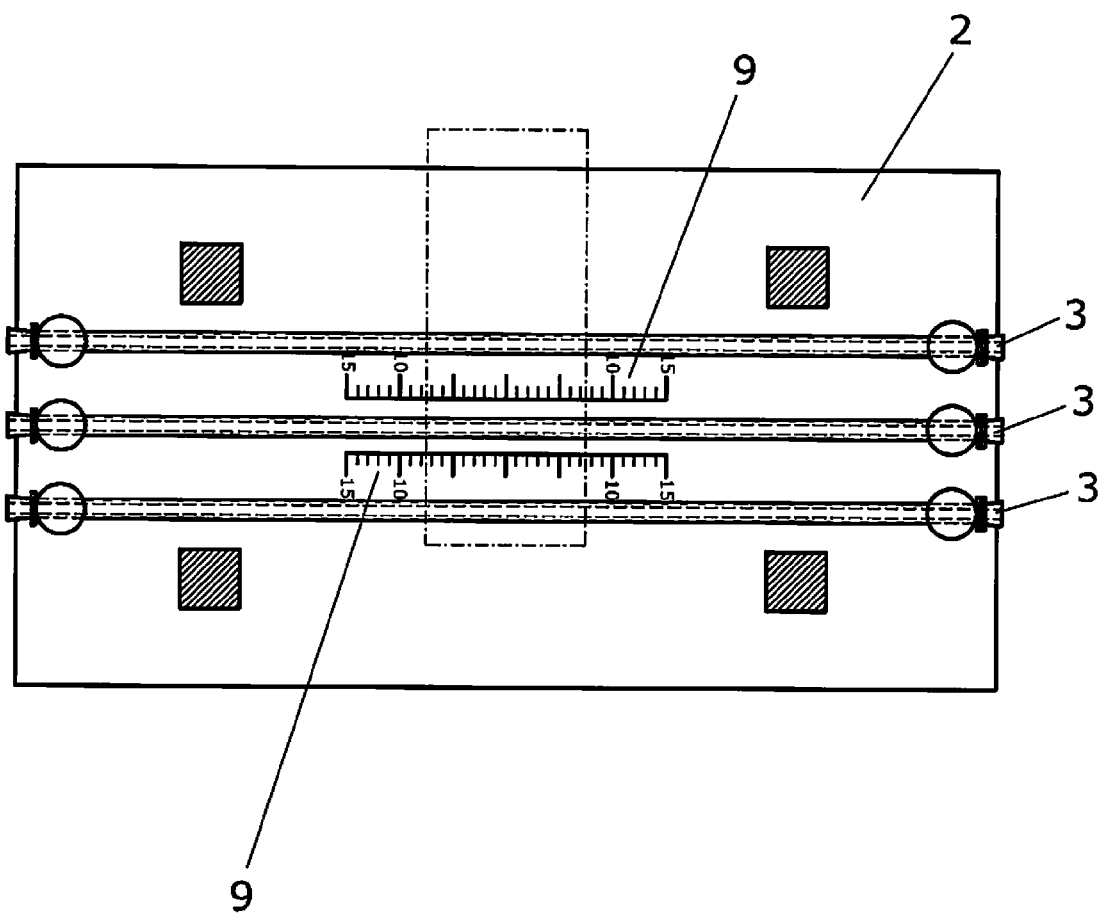
FIG. 3 illustrates a top view of the apparatus with multiple source inserts.

FIG. 3 illustrates a top view of the apparatus with multiple source inserts 3 at the base plate 2. The source inserts 3 allow the user to test multiple afterloader channels in one quality assurance setup. It is well known in the art that afterloaders machines have a plurality of channels. Specifically, afterloader manufacturers like Varian and Nucletron have afterloader machines that contain up to thirty (30) exit source wire ports, also known as channels. Clinical treatments can use more than one afterloader channel, depending on the size and shape of the patient's disease. There can be any number of source inserts 3 on the apparatus; however, only for illustrative purposes we have demonstrated three. During setup of the system, each source inserts 3 will be connected to a single transfer wire. The transfer tube will be connected to the afterloader machine. By having multiple source inserts, the apparatus is able to view multiple source wires and pellets quickly for testing. The calibration points 15 will be used to derive the positional accuracy of all pellet dwell positions. The measurement marker 9 will be used to give the user a visual confirmation of the computer-derived positional accuracy.

Figure 4:
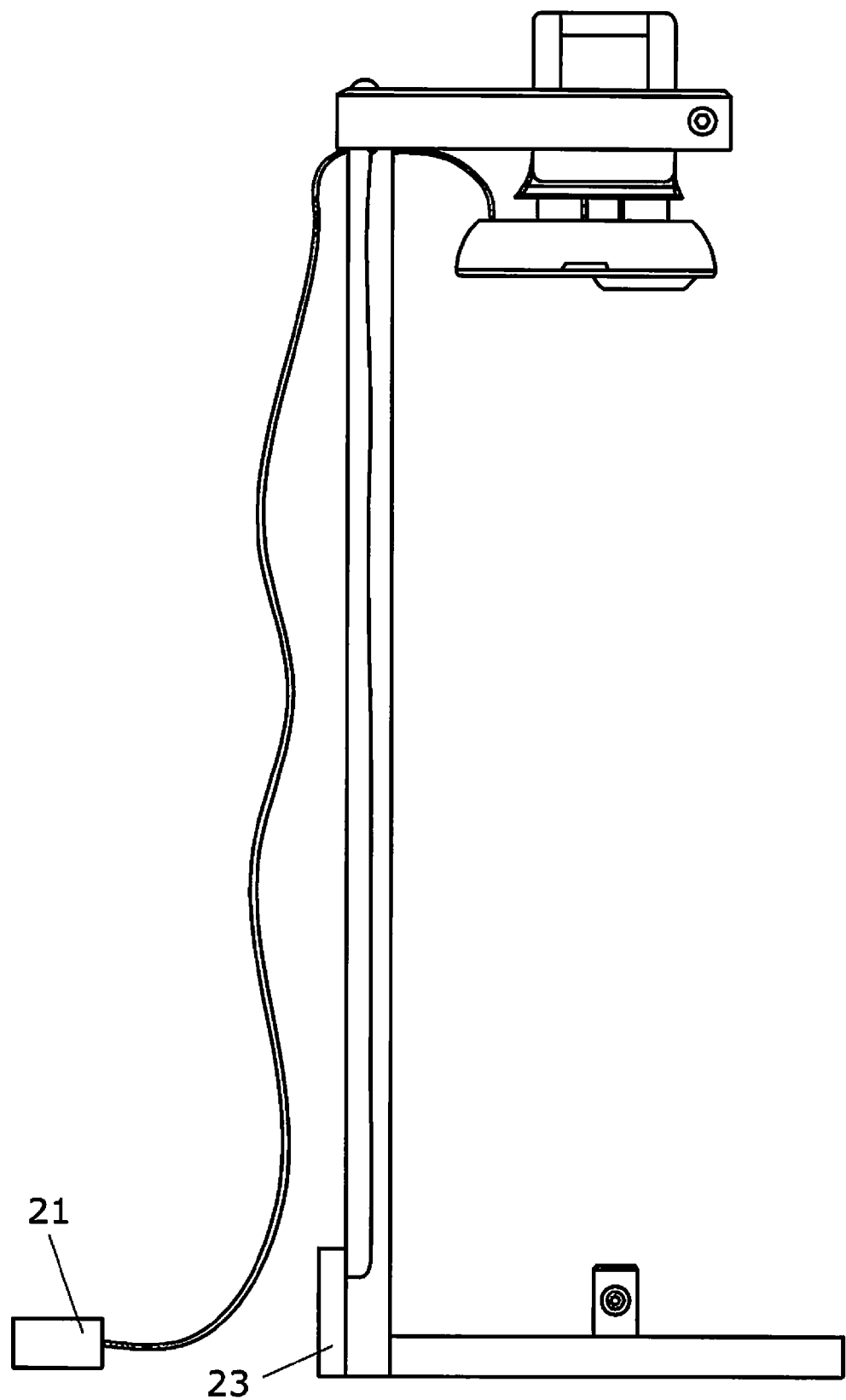
FIG. 4 illustrates a side view of the apparatus.

FIG. 4 illustrates a side view of the apparatus. The apparatus is connected to a battery 23 and a wireless adaptor 21. This figure is used for illustrative purposes only, but should not be limited to; since, the apparatus can be hard-wired to a computer via USB, Cable connection, HDMI, or by serial port. The zoom lens 5 can be a physical lens or a software based focusing algorithm. The battery 23 is used to power the apparatus. The device can also be powered by a number of other sources, including a USB cable, an electric outlet, or solar panels. The measurement ruler 9 can be a physical ruler, a series of markings denoting distances, or simply a physical dimension registered via software. The wireless adaptor 21 is used to communicate to the computer system. This allows for the apparatus to have mobility, and allows for testing in sterile areas of the medical facility. The computer receives the information via wirelessly (via IEEE 802.11a, IEEE 802.11b, IEEE 802.11g, IEEE 802.11n, IEEE 802.16, BlueTooth, HomeRF, HiperLan/1, HiperLan/2, OpenAir, and any future protocols) or wired which then communicates to the computer or any hand-held device.

Figure 5:
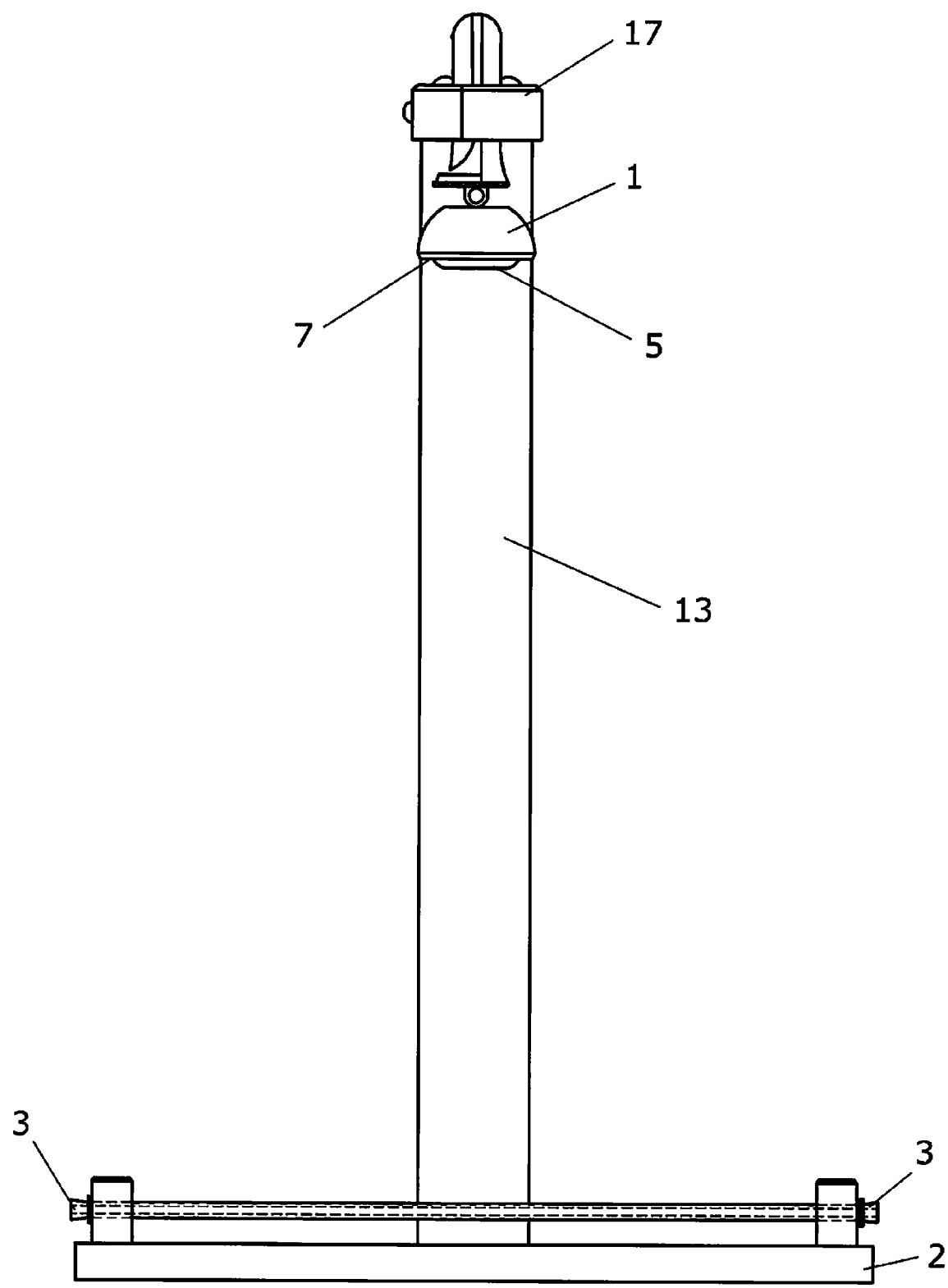
FIG. 5 illustrates a perpendicular front view of the apparatus.

FIG. 5 illustrates a perpendicular front view of the apparatus. The digital camera is located perpendicular from the base plate 2. This provides an advantage since the viewing direction is downwards, which does not reduce visual performance. By changing the angle, the apparatus will produce skewed images and error-prone post-processing corrections would need to be applied, reducing the accuracy and reliability of the results. Many devices behave differently by changing the horizontal and vertical axis, and also require a user to specify the maximum usable viewing angles in both directions. However, the present invention does not require this set, since the apparatus contains a camera lock. Therefore, the perpendicular digital camera is aligned and used to facilitate greater viewing angle in the vertical level and smaller in the horizontal level.

Figure 6:
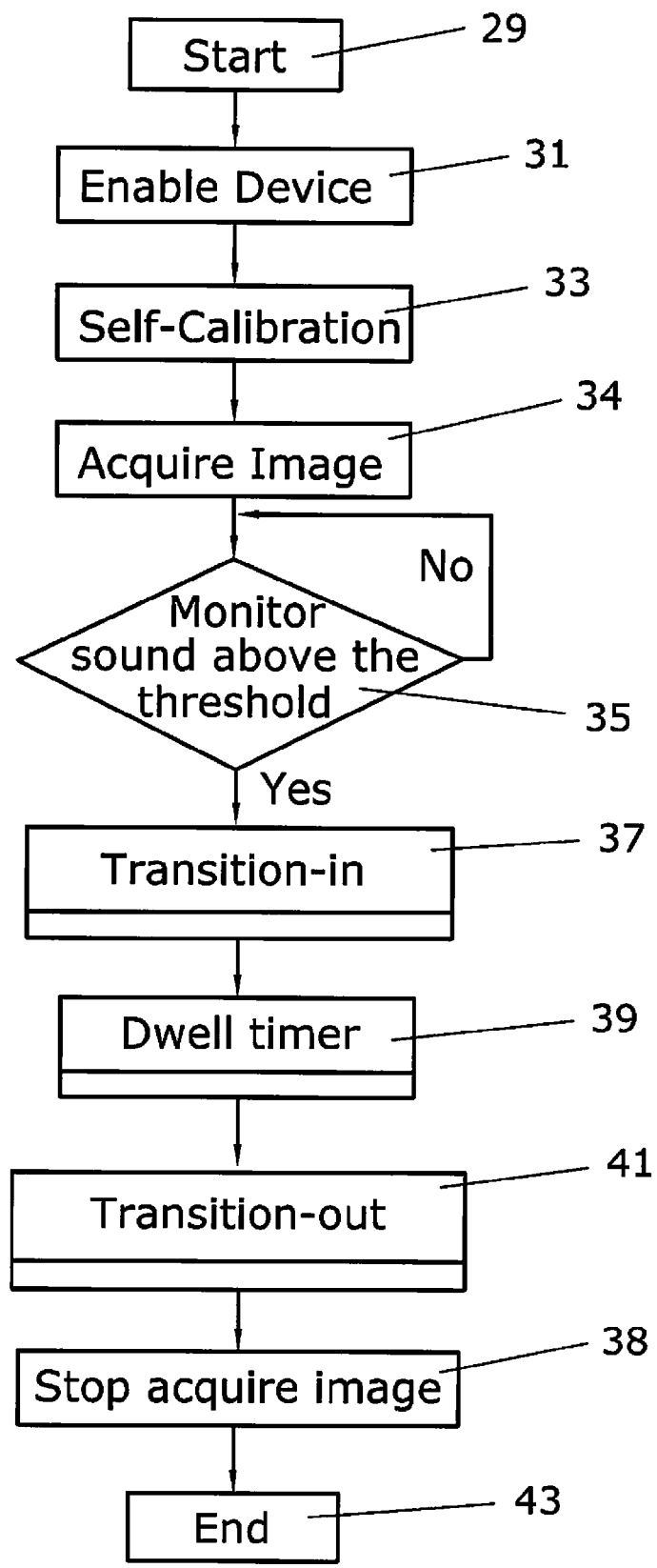
FIG. 6 illustrates a flowchart of an exemplary real-time testing method.

FIG. 6 illustrates a flowchart of an exemplary real-time testing method. The system is connected to the apparatus as demonstrated in FIG. 1. The system begins by enable devices 31. The enablement of devices is to activate the digital camera, lens, light, microphone and the afterloader device. The system will then self-calibrate 33. The self-calibration is done by taking a single image of the source insert to determine that there is enough light, if the camera is position correctly and if the microphone is enabled. The calibration points 15 are then identified, and used to calculate the position of the camera relative to its initial calibration and hence the integrity of the quality assurance device, and consequently the accuracy of the expected measurements. After the self-calibration is complete, the system is active and ready to perform all testing functions. The system starts by acquire images 34. The system takes a plurality of images in real-time. Also, the system has initiated the microphone to determine a sound level threshold. The system will be continuously checking for the sound threshold, if sound level is below the threshold, the system will loop back to itself, as in item 35. Once, the sound level is above the threshold value, such as the sound of the motor in afterloader device used to push the source wire, the system will then indicated that sound level is above the threshold level, and will initiate the transition-in 37. When the transition-in is complete, the dwell timer 39 will begin to start. Next, as soon as the dwell timer 39 is complete, the transition-out 41 will begin. Last, when the transition-out is finished, the system stops to acquire images 38 and then display all the results on a display apparatus. The advantage of present inventions is the process allows for quick testing of an afterloader, after the results are displayed and stored on a computer with the user able to produce copies.

Figure 7:
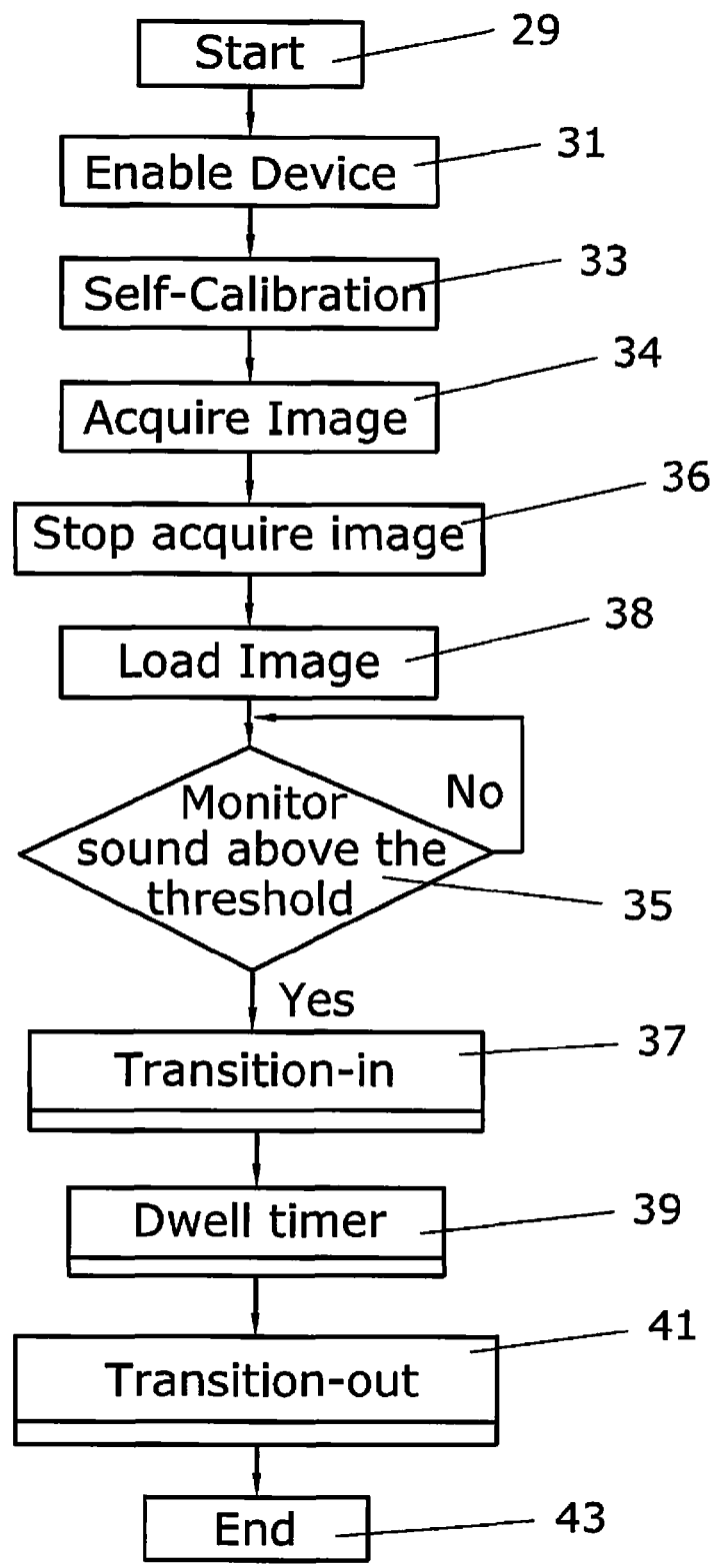
FIG. 7 illustrates a flowchart of an exemplary post-analysis testing method.

FIG. 7 illustrates a flowchart of an exemplary post-analysis testing method. The difference between the real-time and post-analysis is the system in real-time is making the calculations as the afterloader is performing all these steps. In the post-analysis testing, the afterloader will perform the entire step of pushing the source wire, and then holding the source wire, and returning the source wire to the afterloader, which the post-analysis digital camera will store the entire video stream and then perform the analysis thereafter. The advantage for this step is, since real-time image processing is highly processor intensive, when the attached computer is unable to perform real-time analyses due to performance limitations, the stored video stream can be analyzed after the full testing is performed. The post-analysis system begins by enable devices 31. The enablement of devices is to activate the digital camera, lens, light, microphone and the afterloader device. The post-analysis system will then self-calibrate 33. The self-calibration is done by taking a single image of the source insert to determine that there is enough light, if the camera is position correctly and if the microphone is enabled. The calibration points 15 are then identified, and used to calculate the position of the camera relative to its initial calibration and hence the integrity of the quality assurance device, and consequently the accuracy of the expected measurements. After the self-calibration 33 is complete, the post-analysis then acquire image 34. After the system has completed collecting the images, the post-analysis then stop acquire image 36. Then, the system loads the image 38 and begins analysis. After loading the images with sound information, the system then monitors sound to reach above the threshold value 35 within the data files. Once the threshold value has been reached the post-analysis system then begins the transition in 37. When the transition-in is complete, the dwell timer 39 will begin to start. Next, as soon as the dwell timer 39 is complete, the transition-out 41 will begin. Last, when the transition-out 41 is finished, the system stops to analyze image 38 and then displays all the results on a display apparatus. This leads to the advantage of a cost effective system that reports problems with an afterloader and satisfies all state and federal laws regarding the regular testing of afterloader devices.

Specifically, with the real-time and post-analysis systems, the transition-in, dwell timer, and transition-out are performed nearly the same way. Thus, hereafter, the functionality of the transition-in, dwell timer and transition-out will be discussed in greater detail below. The advantage of having a real-time or post-analysis system, allows the medical facility to test quickly an afterloader device since there would be not film development as well as film analysis; and thus, providing an increased accuracy of the results.

Figure 8:
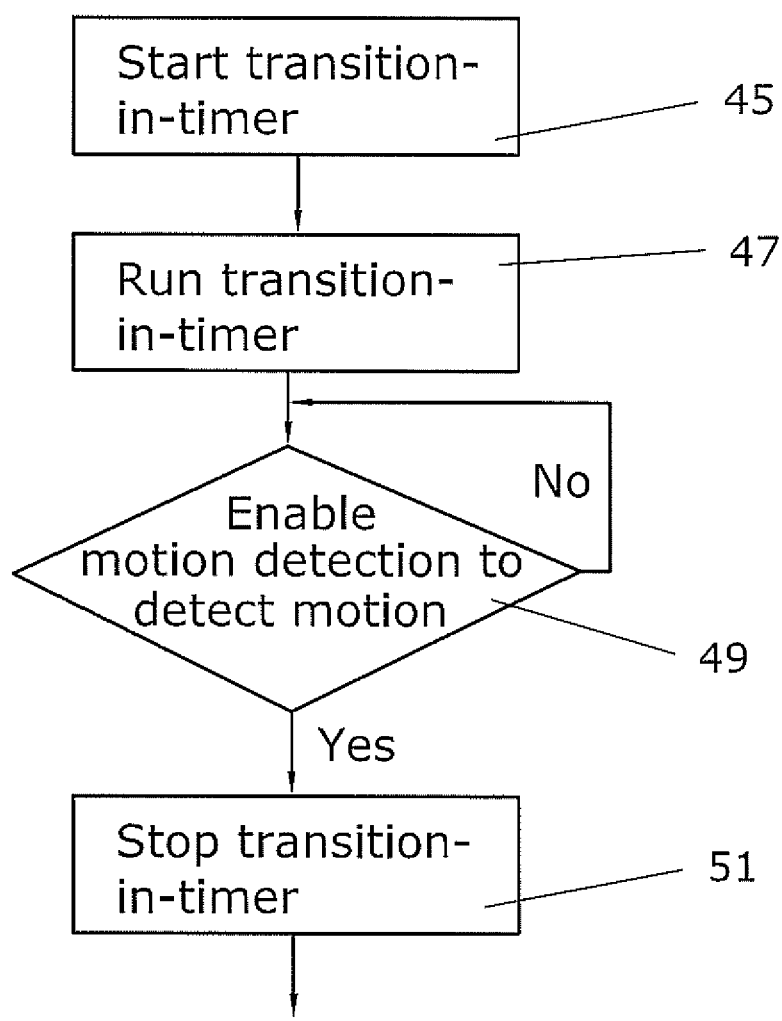
FIG. 8 illustrates a flowchart of an exemplary transitions-in method.

FIG. 8 illustrates a flowchart of an exemplary transition-in method. The transition-in-timer 45 is initiated. The run transition-in-timer 47 is the running of the timer. The timer will run until a function has been performed. The transition-in-timer will keep running 47 until the digital camera 1 detects motion 49. The motion is detected when the source wire and pellet in the source insert 3 reach near the center of the base plate 2. Once the source wire and pellet have stopped moving forward, the system then stops the transition-in-timer 51 and records the amount of time that the source wire and pellet took to reach its destination. This transit time is useful in assessing any extra dose to the patient due to the source transitioning between the source vault in the afterloader machine or afterloader device to inside the patient. Also, having the digital camera 1 analyze the source wire and pellet, by this type of system check, allows users to verify that the source wire and radioactive pellet are actually in the patient during their treatment. After stopping the transition-in-timer, the system moves to the next step of dwell timer.

Figure 9:
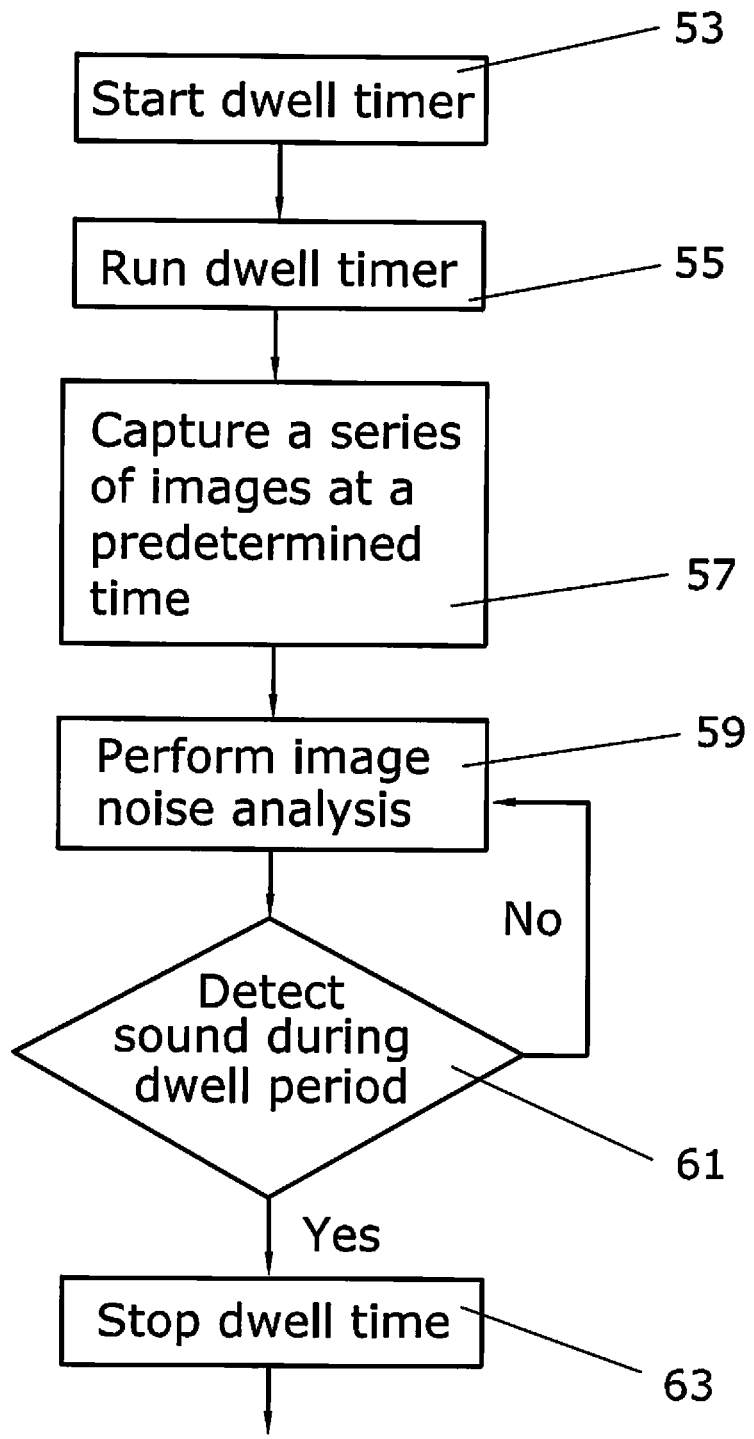
FIG. 9 illustrates a flowchart of an exemplary dwell time method.

FIG. 9 illustrates a flowchart of an exemplary dwell time method. Once the system has stopped the transition-in-timer, the system begins the dwell timer. The system runs the dwell timer and starts to capture a series of images within a predetermined time interval. The system captures the images and performs measurements on the source wire and pellet by comparing it to the measured ruler on the base plate. Depending on the location of the source wire and pellet, for example if the source wire and pellet are 0.5 mm to 2.0 mm from the ideal location, scheduled treatments can be timely interrupted to prevent mistreatments. The manual adjustments can be made by a technician to recalibrate the motor on the afterloader device. Next, while the dwell timer is running, the system will then also perform an image noise analysis 59. The image noise analysis is used to determine the strength or activity of the pellet. The image noise analysis is done by determining the level of white noise at the calibration points. The level of noise is then correlated to a premeasured level, and an activity is calculated from the ratio of the current noise level to the premeasured level. Then, the system detects for sound to reach over a threshold level 61. The threshold for the sound can be met when the after load motor starts to pull the source wire and pellet back into the afterloader device. Once the sound threshold level is set, the dwell timer stops 63. The dwell timer is used to measure the amount of time that the source wire and pellet are in the patient. This provides an advantage to confirm the accuracy of the afterloader's programmed times, as required by state and federal regulations.

Figure 10:
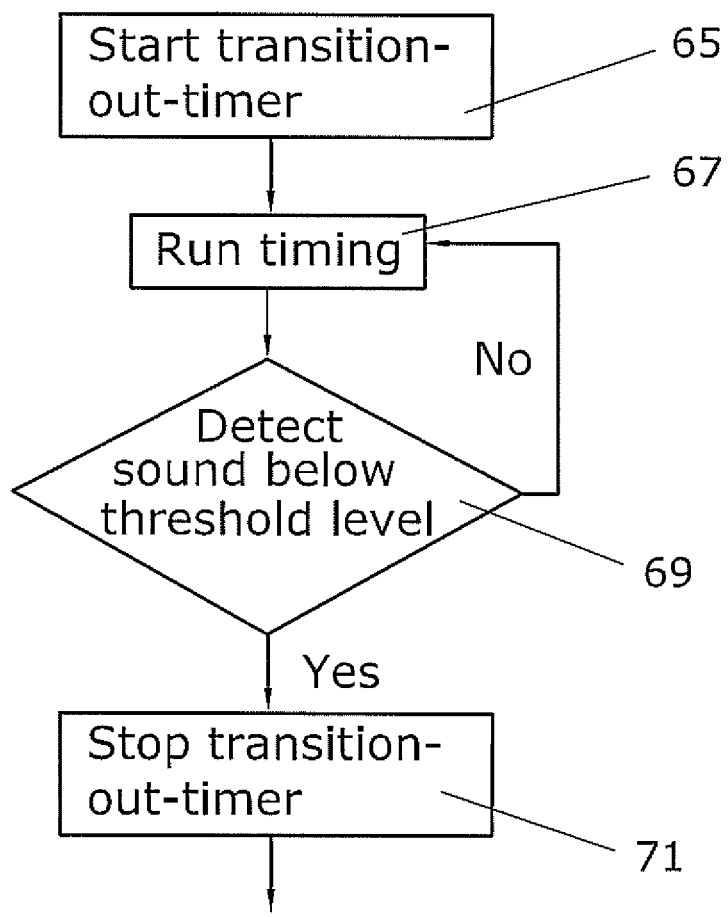
FIG. 10 illustrates a flowchart of an exemplary transitions-out.

FIG. 10 illustrates a flowchart of an exemplary transition-out. The transition-out-timer starts 65 as soon as the dwell timer has ended. The transition-out-timer runs 67 until the system determines when the sound level is below a threshold value 69. An example for the system to reach this threshold value is when the afterloader terminates the motor to pull the source wire and pellet back to the machine. Once the sound level is reached, the system will stop the transition-out-timer 71.

Once the system has analyzed and calculated the transition-in times, transition-out times, dwell times, source activity, and dwell position accuracy, the system will display this information on a computer apparatus. Additionally, the results are stored on the computer, and the user is opted to produce a hard copy. Specifically, the information can be compared to previous analyses for consistency. The advantage for using the information is as follows. The system can make a comparison between the transition-in-timer and transition-out-timer over a period of time to see if a trend exists. The system can record each test and provide a printable report of each time and segment.

Figure 11:
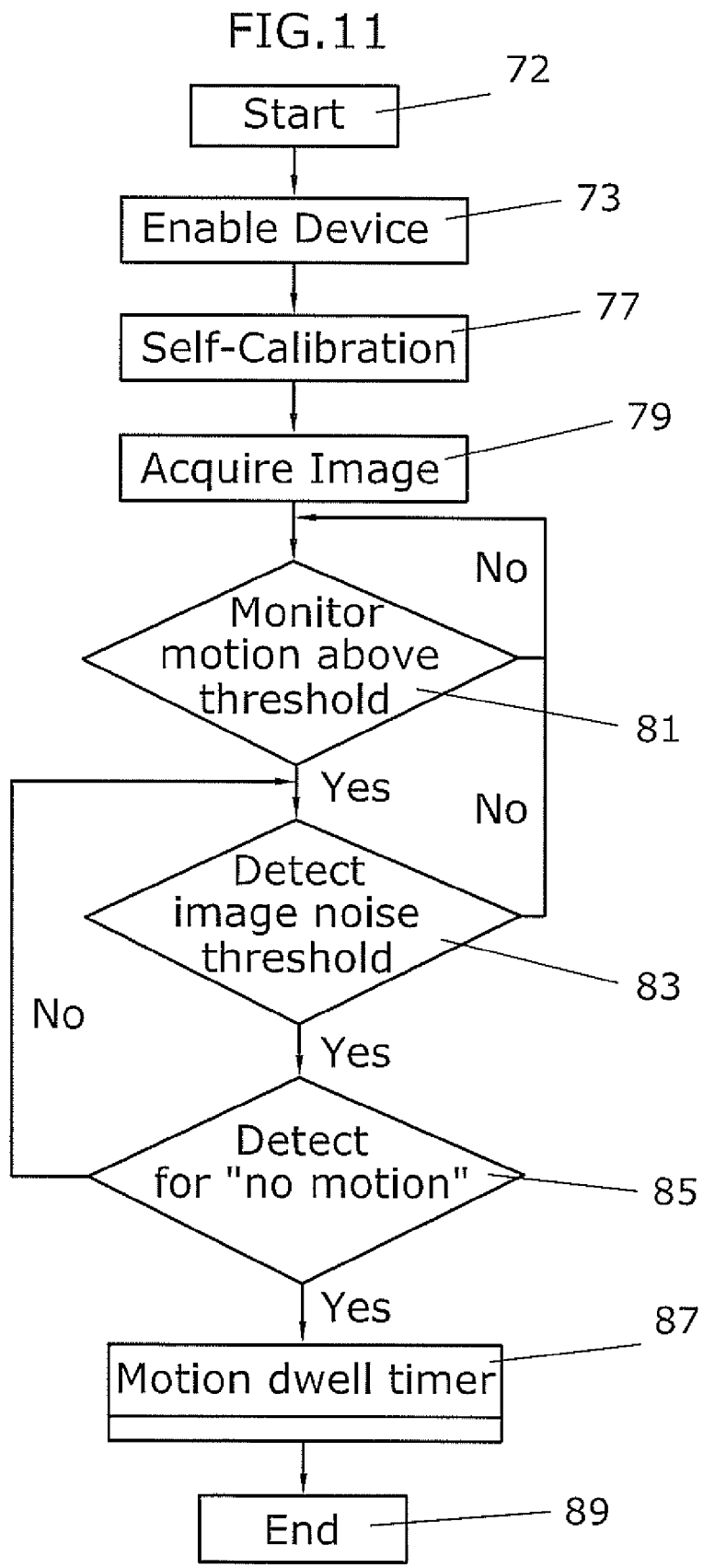
FIG. 11 illustrates a flowchart of an exemplary multiple dwell mode.

FIG. 11 illustrates a flowchart of an exemplary multiple dwell mode. The multiple dwell mode is when there are multiple programmed dwell positions within source insert tube 3. Each programmed position will dwell at a specific location for a specific time, a dwell time, when inside the source insert 3. The multiple dwell mode starts 72 and is initiated by first enabling the device 73. The system begins a self-calibration 77 and thereafter begins to acquire images 79. The image can be stored in the system or may be captured in real-time by the camera. When the system acquires the images, the system starts to monitor for motion above a threshold value 81. If no motion is detected, the system loops back and continuously checks to determine if there is motion. When there is motion, the system will then determine the image noise 83. The average pixel value and variance in pixel value are determined around the four black squares 15, and is analyzed to determine whether image noise is being caused by the proximity of the radioactive source to the base plate 2, and hence determine that the brachytherapy source has exited the vault of the afterloader. The purpose of this analysis is to determine whether any detected motion is due to the dummy wire or to the source. The system then determines if there is no motion 85. When the system determines there is no motion, this indicates that the source has reached the programmed location. If the system does detect motion, then the system is determining image noise 83 and then the system loops back to determine if there is no motion 85. By continuously checking for image noise, the system is making sure that there is a radioactive source. When there is no motion, the system begins the motion dwell timer 87, as illustrated further in FIG. 12. After the timer is complete and the source retracted into the afterloader vault, the system ends the process and displays all the results 89.

Figure 12:
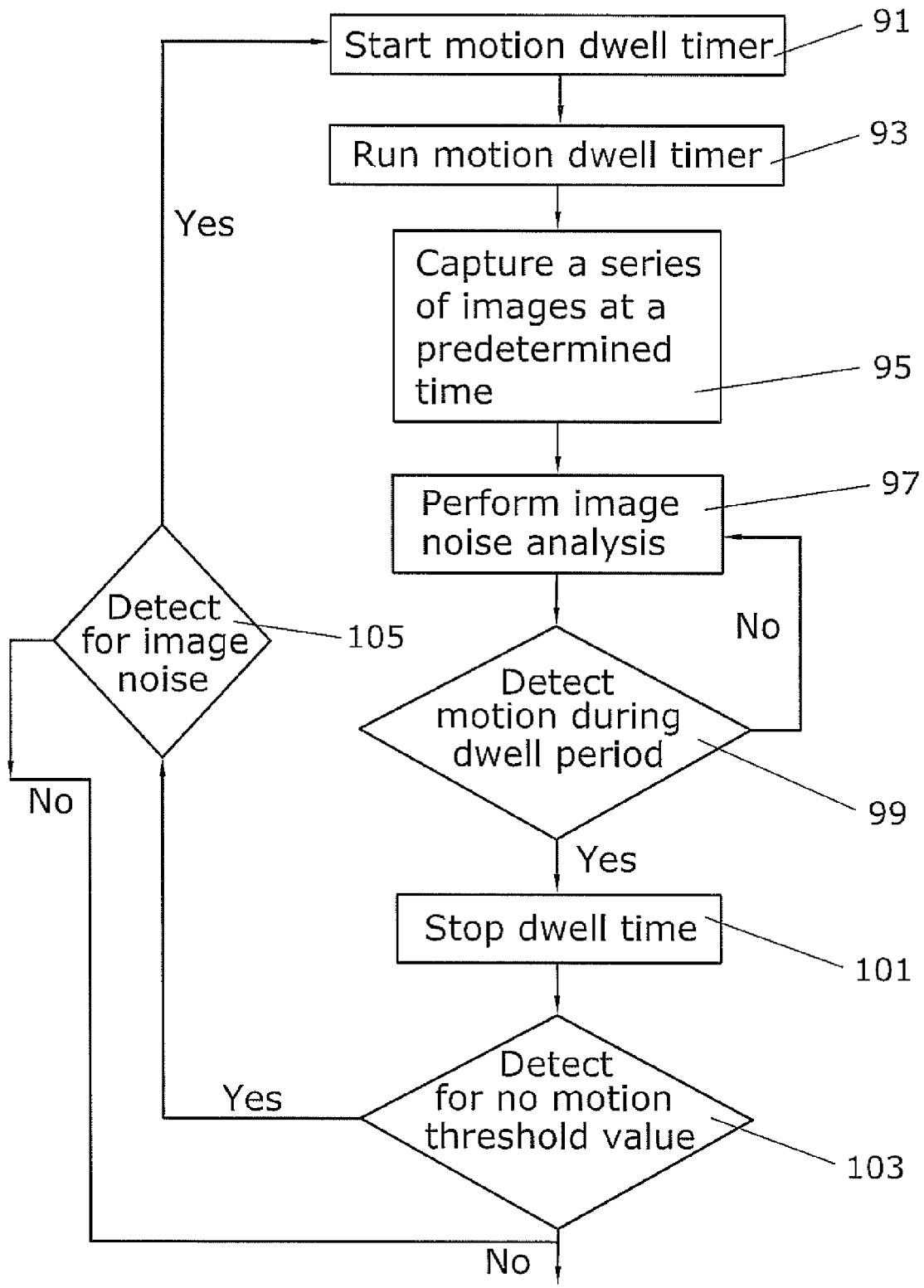
FIG. 12 illustrates a flowchart of an exemplary timer for multiple dwell mode.

FIG. 12 illustrates a flowchart of an exemplary timer for a multiple dwell mode. The system begins by starting the motion dwell timer 91. The system begins by activating the timer 93. The system then captures a series of images at a predetermined interval 95 and then performs an image noise analysis 97. The image noise analysis is used to verify that there is a radioactive source in the source insert tube 3. Then the system determines to see if there is motion by the radioactive source 99. If there is a radioactive source that starts to move, then the system turns the dwell timer off 101. If the system determines there is no movement, it continues to check for motion. The system then records all the information. Then, the system detects for no motion to determine that the radioactive source has returned back to the starting position 103. The system, once again, detects if there is image noise 105. If the system determines that there is image noise above a threshold level, then the system knows that there is another programmed dwell position to analyze inside the source insert tube 3, and then loops back to the start motion dwell timer for the dwell positions. However, if the system does not detect image noise, the system deduces the source has been retracted back into the afterloader's vault.

Figure 13:
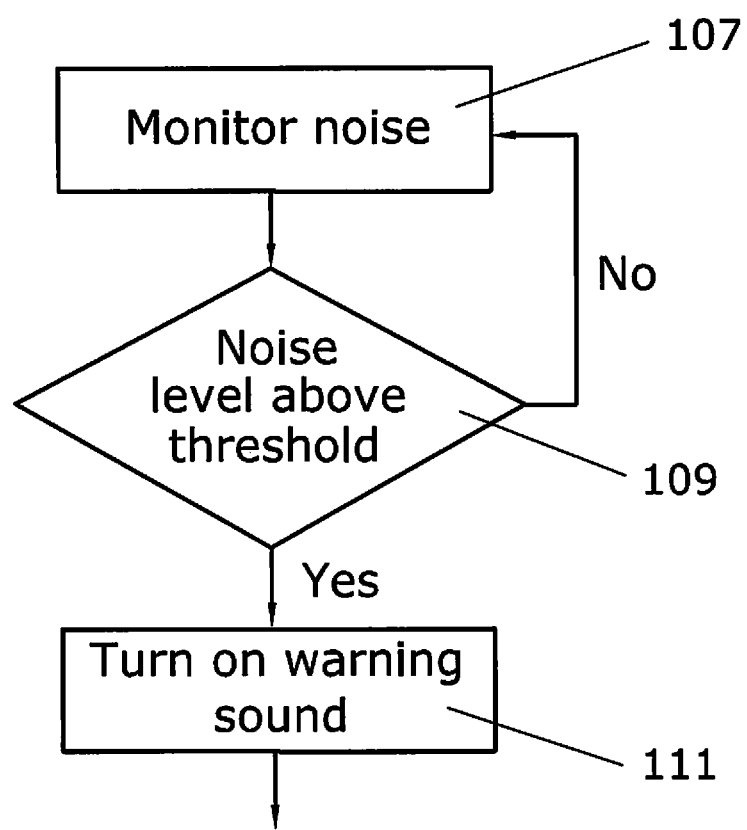
FIG. 13 illustrates a flowchart of an exemplary warning system for the afterloader apparatus.

FIG. 13 illustrates a flowchart of an exemplary alarm warning system for an afterloader apparatus. Specifically, the system will monitor the noise 107. Then the system determines if the noise were to reach a threshold level 109. The threshold level can be reached when the sound of the motor is pushing the radioactive source out or in. Once the system is reaches the threshold level, a warning sound will be alarmed out 111. The alarm is used to provide patient protection and notify medical personnel of manufacturing defects.

The invention claimed is:

1. An apparatus for calibrating a high-dose-rate afterloader machine, comprising:
   an image capturing device adapted to capture a plurality of still images or a real-time video from visible light, said image capturing device having a visual field of view, said image capturing device including a camera configured to capture the images or the real-time video in said visual field of view from said visible light, a microphone configured to detect sound levels corresponding to operation of said afterloader machine, wherein the captured images or the captured real time video and the detected sound levels provide information corresponding to at least one position of a radioactive source associated with said afterloader machine;
   a base plate within said visual field of view of said image capturing device;
   a plurality of calibration points located on said base plate within said visual field of view for identification by said image capturing device;
   at least one source insert, positioned on said base plate and configured to be communicatively connected to said afterloader machine, said at least one source insert being configured to position a radioactive pellet from said afterloader machine on said base plate by entry into a corresponding source insert of the at least one source insert, wherein said radioactive pellet comprises said radioactive source that is communicatively connected to a source wire configured to position the corresponding radioactive pellet on said base plate, wherein the corresponding radioactive pellet when positioned on said base plate is visible from said visible light to image capture by said image capturing device; and
   an adjustable shaft that is connected to said base plate and connected to said image capturing device to support said image capturing device above said base plate.

2. The apparatus for calibrating a high-dose-rate afterloader machine according to claim 1, further comprising:
   a plurality of source inserts,
   wherein said image capturing device simultaneously or individually makes measurements corresponding to a position for each of said plurality of source inserts.

3. The apparatus for calibrating a high-dose-rate afterloader machine according to claim 2, wherein:
   said image capturing device communicates with said microphone, and
   information provided from both said camera and said microphone is used to adjust said afterloader machine.

4. The apparatus for calibrating a high-dose-rate afterloader machine according to claim 1, further comprising:
   a battery,
   wherein said battery is connected to said image capturing device; and
   a wireless transmitter, wherein said wireless transmitter communicates all information from said image capturing device to a computer apparatus for analysis.

5. The apparatus for calibrating a high-dose-rate afterloader machine according to claim 1, wherein an alarm sound is associated with a threshold level of noise corresponding to operation of said afterloader machine.

6. The apparatus for calibrating a high-dose-rate afterloader machine according to claim 1, further comprising:
   a measurement ruler located on said base plate positioned in relation to said at least one source insert and visible to said image capturing device to measure a position of the corresponding source wire and the corresponding radioactive pellet.

7. The apparatus for calibrating a high-dose-rate afterloader machine according to claim 1, wherein said at least one source insert comprises a source insert tube.

8. The apparatus for calibrating a high-dose-rate afterloader machine according to claim 1, wherein said image capturing device is associated with means for processing images captured by said image capturing device.

9. The apparatus for calibrating a high-dose-rate afterloader machine according to claim 8, wherein said image capturing device further is associated with means for acquiring and analyzing information obtained by processing images captured by said image capturing device.

10. The apparatus for calibrating a high-dose-rate afterloader machine according to claim 1, further comprising:
    a computer communicating with said image capturing device for processing images captured by said image capturing device.

11. The apparatus for calibrating a high-dose-rate afterloader machine according to claim 10, wherein said computer acquires and analyzes information obtained by processing images captured by said image capturing device.

12. The apparatus for calibrating a high-dose-rate afterloader machine according to claim 10, wherein said computer monitors sound levels detected by said microphone and determines whether the sound levels detected by said microphone are above or below a sound level threshold.

13. The apparatus for calibrating a high-dose-rate afterloader machine according to claim 1, further comprising:
    a light source to provide said visible light.

14. An apparatus for calibrating a high-dose-rate afterloader machine, comprising:
    an image capturing device adapted to capture a plurality of still images or a real-time video from visible light, said image capturing device having a visual field of view, said image capturing device including a camera configured to capture the images or the real-time video in said visual field of view from said visible light, a microphone configured to detect sound levels corresponding to operation of said afterloader machine, wherein the captured images or the captured real time video and the detected sound levels provide information corresponding to at least one position of a radioactive source associated with said afterloader machine;
    a base plate within said visual field of view of said image capturing device;
    a plurality of calibration points located on said base plate within said visual field of view for identification by said image capturing device;
    at least one source insert, positioned on said base plate and configured adapted to be communicatively connected to said afterloader machine, said at least one source insert being configured to position a radioactive pellet from said afterloader machine on said base plate by entry into a corresponding source insert of said at least one source insert, wherein said radioactive pellet comprises said radioactive source that is communicatively connected to a source wire configured to position the corresponding radioactive pellet on said base plate, wherein said corresponding radioactive pellet when positioned on said base plate is visible from said visible light to image capture by said image capturing device;

an adjustable shaft that is connected to said base plate and connected to said image capturing device to support said image capturing device above said base plate;

a transition-in-timer adapted to start timing when a sound level detected by said microphone is above a predetermined threshold value and to stop timing when said image capturing device detects a stop in movement of the corresponding radioactive pellet associated with said afterloader machine to determine a time period corresponding to a transition-in time of the corresponding radioactive pellet to move to a position;

a dwell timer adapted to start timing when said transition-in-timer stops timing and to stop timing when a sound level detected by said microphone is above a predetermined threshold value to determine a time period corresponding to a dwell time of the corresponding radioactive pellet at a position; and a transition-out-timer adapted to start timing when said dwell timer has stopped timing and to stop timing when a sound level detected by said microphone is below a predetermined threshold value to determine a time period corresponding to a transition-out time of the corresponding radioactive pellet to move from a position.

15. An apparatus for calibrating a high-dose-rate afterloader device, comprising:

an image capturing device adapted to capture a plurality of images from visible light, said image capturing device having a visual field of view, said image capturing device including a visual detector configured to capture the images in said visual field of view from said visible light and including a sound detector configured to detect sound levels corresponding to operation of said afterloader device, wherein the captured images and the detected sound levels provide information corresponding to at least one position of a radioactive source associated with said afterloader device;

a base plate adapted to be positioned within said visual field of view of said image capturing device; and a source insert positioned on said base plate and configured to communicatively connect to said afterloader device, said source insert being configured to position said radioactive source from said afterloader device on said base plate by entry into said source insert, and wherein said radioactive source when positioned on said base plate is visible from said visible light to image capture by said image capturing device to determine at least one position of said radioactive source.

16. The apparatus for calibrating a high-dose-rate afterloader device according to claim 15, further comprising:

a plurality of calibration points located on said base plate within said visual field of view for identification by said image capturing device to determine a position of said visual detector relative to an initial calibration of said visual detector.

17. The apparatus for calibrating a high-dose-rate afterloader device according to claim 16, wherein said visual detector comprises a camera and said sound detector comprises a microphone.

18. The apparatus for calibrating a high-dose-rate afterloader device according to claim 15, wherein said visual detector comprises a camera and said sound detector comprises a microphone.

19. The apparatus for calibrating a high-dose-rate afterloader device according to claim 15, wherein:

said source insert comprises a plurality of source inserts positioned on said base plate and configured to be communicatively connected to said afterloader device, said plurality of source inserts each being configured to position a corresponding said radioactive source from said afterloader device on said base plate, wherein a corresponding said radioactive source when positioned on said base plate is visible from said visible light to image capture by said image capturing device.

20. The apparatus for calibrating a high-dose-rate afterloader device according to claim 15, further comprising:

an adjustable shaft that is connected to said base plate and connected to said image capturing device to support said image capturing device above said base plate.

21. The apparatus for calibrating a high-dose-rate afterloader device according to claim 20, further comprising:

a plurality of calibration points located on said base plate within said visual field of view for identification by said image capturing device to determine a position of said visual detector relative to an initial calibration of said visual detector.

22. An apparatus for calibrating a high-dose-rate afterloader device, comprising:

an image capturing device adapted to capture a plurality of images from visible light, said image capturing device having a visual field of view, said image capturing device including a visual detector configured to capture the images in said visual field of view from said visible light and including a sound detector configured to detect sound levels corresponding to operation of said afterloader device, wherein the captured images and the detected sound levels provide information corresponding to at least one position of a radioactive source associated with said afterloader device;

a base plate adapted to be positioned within said visual field of view of said image capturing device;

a source insert positioned on said base plate and configured to communicatively connect to said afterloader device, said source insert being configured to position said radioactive source from said afterloader device on said base plate by entry into said source insert, and wherein said radioactive source when positioned on said base plate is visible from said visible light to image capture by said image capturing device to determine at least one position of said radioactive source;

a transition-in-timer adapted to start timing when a sound level detected by said sound detector is above a predetermined threshold value and to stop timing when said visual detector detects a stop in movement of said radioactive source associated with said afterloader device to determine a time period corresponding to a transition-in time of said radioactive source to move to a position;

a dwell timer adapted to start timing when said transition-in-timer stops timing and to stop timing when a sound level detected by said sound detector is above a predetermined threshold value to determine a time period corresponding to a dwell time of said radioactive source at a position; and a transition-out-timer adapted to start timing when said dwell timer has stopped timing and to stop timing when a sound level detected by said sound detector is below a predetermined threshold value to determine a time period corresponding to a transition-out time of said radioactive source to move from a position.

23. An apparatus for calibrating a high-dose-rate afterloader device, comprising:

an image capturing device adapted to capture a plurality of images from visible light, said image capturing device having a visual field of view, said image capturing device including a visual detector configured to capture the images in said visual field of view from said visible light and including a sound detector configured to detect sound levels corresponding to operation of said afterloader device, wherein the captured images and the detected sound levels provide information corresponding to at least one position of a radioactive source associated with said afterloader device;

a base plate adapted to be positioned within said visual field of view of said image capturing device;

one or more source inserts positioned on said base plate and configured to communicatively connect to said afterloader device, said one or more source inserts each being configured to position a corresponding said radioactive source from said afterloader device on said base plate by entry into a corresponding said source insert, and wherein the corresponding said radioactive source when positioned on said base plate is visible from said visible light to image capture by said image capturing device to determine at least one position of the corresponding said radioactive source;

a transition-in-timer adapted to start timing when a sound level detected by said sound detector is above a predetermined threshold value and to stop timing when said visual detector detects a stop in movement of the corresponding said radioactive source associated with said afterloader device to determine a time period corresponding to a transition-in time of the corresponding said radioactive source to move to a position;

a dwell timer adapted to start timing when said transition-in-timer stops timing and to stop timing when a sound level detected by said sound detector is above a predetermined threshold value to determine a time period corresponding to a dwell time of the corresponding said radioactive source at a position; and a transition-out-timer adapted to start timing when said dwell timer has stopped timing and to stop timing when a sound level detected by said sound detector is below a predetermined threshold value to determine a time period corresponding to a transition-out time of the corresponding said radioactive source to move from a position.

\* \* \* \* \*